United States Patent [19]

Fishman et al.

[11] Patent Number: 5,318,680

[45] Date of Patent: Jun. 7, 1994

[54] ON-COLUMN DERIVATIZATION IN CAPILLARY ELECTROPHORESIS

[75] Inventors: Harvey A. Fishman, Stanford; Jason B. Shear; Luis A. Colon, both of Menlo Park; Richard N. Zare, Stanford, all of Calif.; Jonathan V. Sweedler, Champaign, Ill.

[73] Assignee: Board of Trustees of the Leland Stanford Junior University, Stanford, Calif.

[21] Appl. No.: 847,176

[22] Filed: Mar. 6, 1992

Related U.S. Application Data

[63] Continuation-in-part of Ser. No. 235,953, Aug. 24, 1988, abandoned.

[51] Int. Cl.⁵ .................... G01N 27/26; G01N 27/447
[52] U.S. Cl. .............................. 204/180.1; 204/299 R
[58] Field of Search ......................... 204/180.1, 299 R

[56] References Cited

U.S. PATENT DOCUMENTS 5,045,172  9/1991  Guzman .......................... 204/299 R
5,110,431  5/1992  Moring ............................. 204/180.1

OTHER PUBLICATIONS

Stephen L. Pentoney, Jr. et al., "On-Line Connector for Microcolumns: Application to the On-Column o-Phthaldialdehyde Derivatization of Amino Acids Separated by Capillary Zone Electrophoresis", Analytical Chemistry, vol. 60, No. 23 (Dec. 1, 1988) 2625-2629.

Richard M. Caprioli et al., "Coupling Cappillary zone Electrophoresis and Continuous-Flow Fast Atom Bombardment Mass Spectrometry for the Analysis of Peptide Mixtures", Journal of Chromatography, 480 (1989).

U. R. Tjaden, N. J. Reinhoud, and J. Vander Greef, "On-Line Derivatization In High Performance Capillary Electrophoresis", poster presentation at The Thirteenth Symposium on Column Liquid Chromatography, Stockholm, Sweden, Jun. 25-30, 1989.

"A Polymeric Reagent for Derivatization of Weak Nucleophiles in HPLC-UV", by Bourque and Krull, Journal of Chromatographic Science, 29:489-496, Nov. 1991.

"The Use of a Concentration Step to Collect Urinary Components Separated by Capillary Electrophoresis . . . ", by Guzman et al., Journ. of Liq. Chromatography 14(5):997-1015, 1991.

"The Use of On-Line Sample Concentration to Increase the Sensitivity of Capillary Electrophoresis", presented by Merion, et al., Mass. HPCE'91.

"Solid-Phase Reagent Containing the 3,5-Dinitrophenyl Tag for the Improved Derivatization of Chiral and Achiral Amines, . . . ", by Bourque et al., Journal of Chromatography, 537:123-152, 1991.

"On-Line Connector for Microcolumns: Application to the On-Column o-Phthaldialdehyde Derivatization of . . . ", by Pentoney, Jr. et al., Anal. Chem., 60:2625-2629, 1988.

"Capillary Isoelectric Focusing of Proteins in Uncoated Fused-Silica Capillaries Using Polymeric . . . ", by Mazzeo et al., Anal. Chem., 63:2852-2857, 1991.

"On-Line Derivatization in High Performance Capillary Electrophoresis", by Tjaden, et al., The Netherlands.

Patent Application Ser. No. 07/235,953 filed Aug. 24, 1988.

Primary Examiner—John Niebling
Assistant Examiner—John S. Starsiak, Jr.
Attorney, Agent, or Firm—Majestic, Parsons, Siebert & Hsue

[57] ABSTRACT

An on-column derivatization scheme where a liquid or solid labeling reagent is provided in a capillary to react chemically with a sample in order to label the sample. Electrophoretic separation may be carried out immediately thereafter to simplify the derivatization, separation and detection process. By localizing the labeling process to a small area within the capillary, fast kinetics and high reaction yield are achieved.

37 Claims, 5 Drawing Sheets

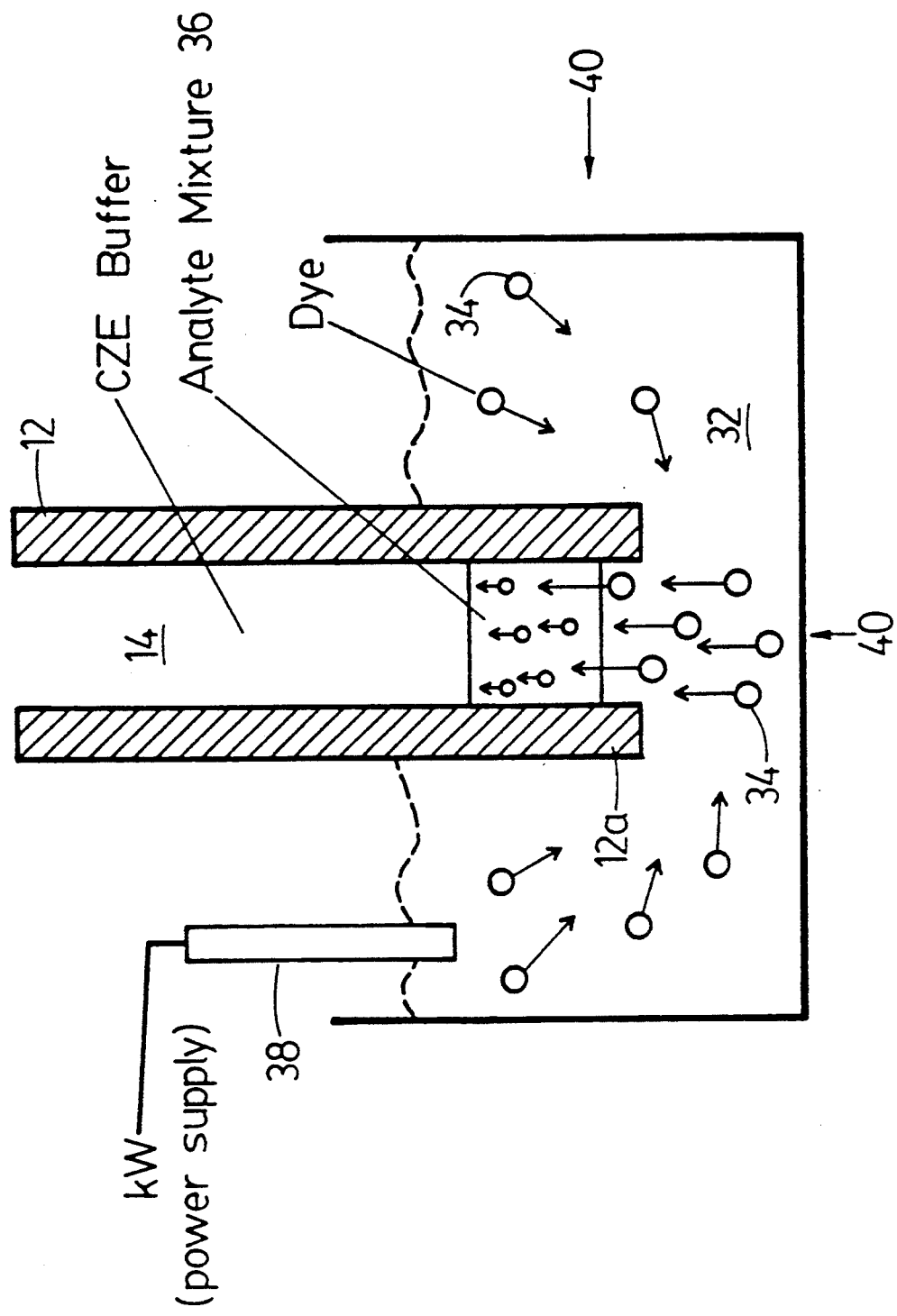
FIG._2.

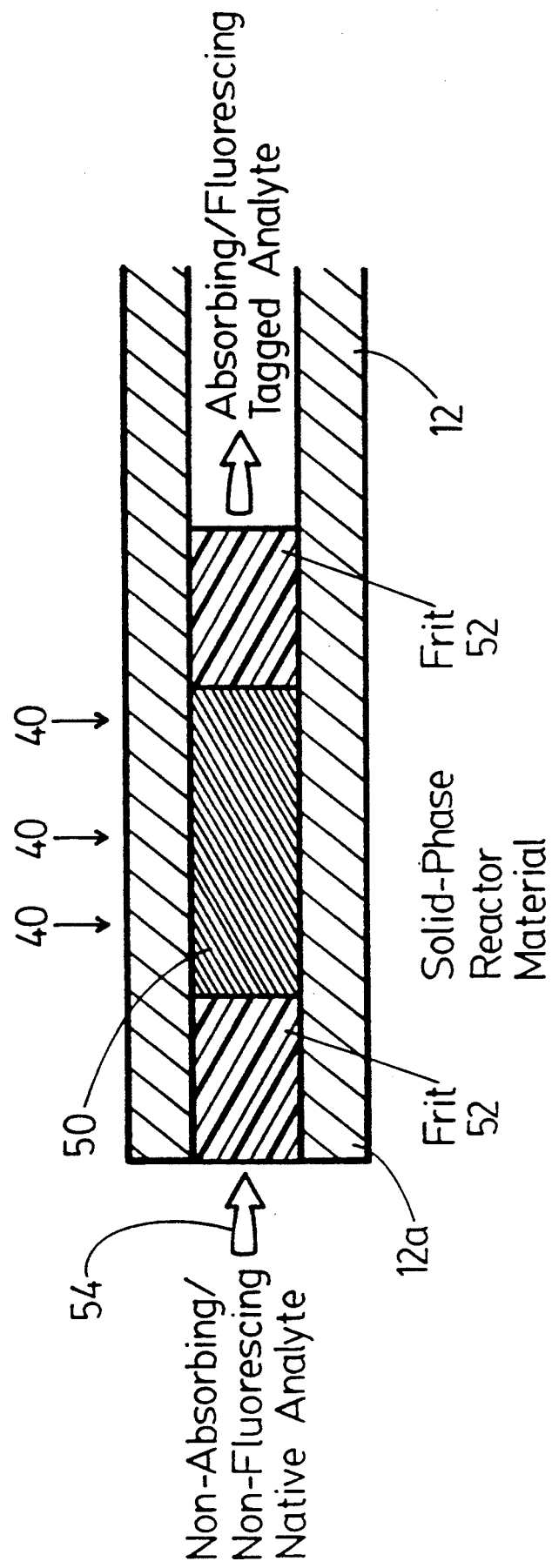
FIG._3.

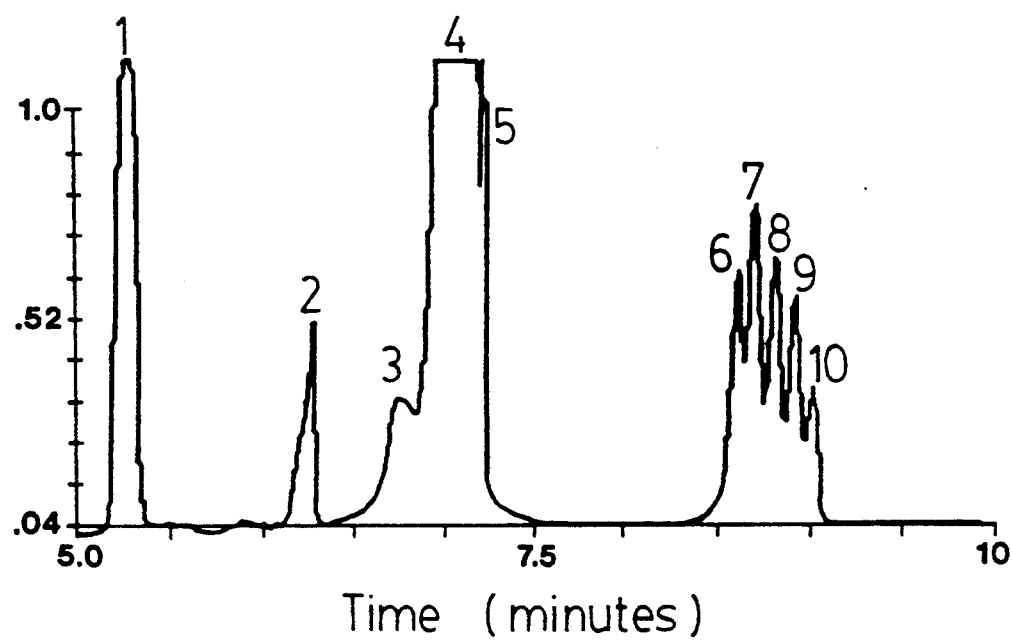
FIG._4.
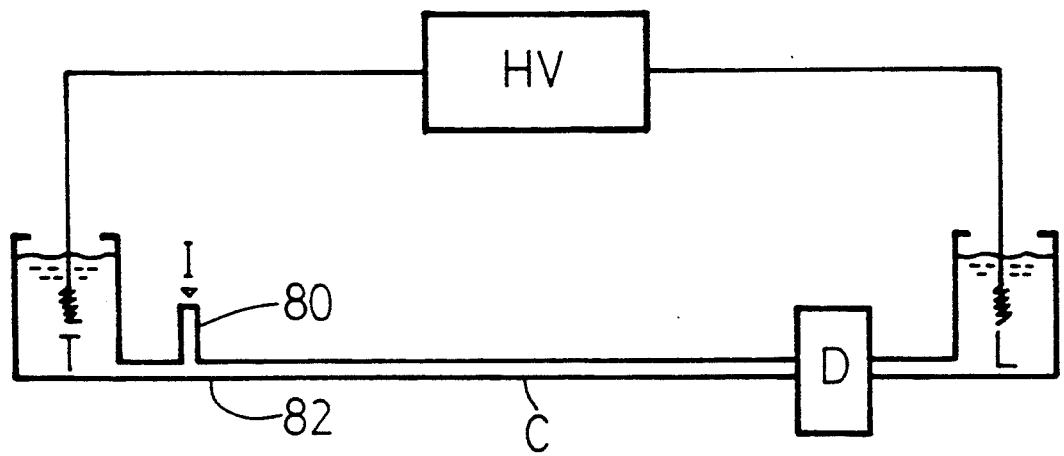
FIG._5.

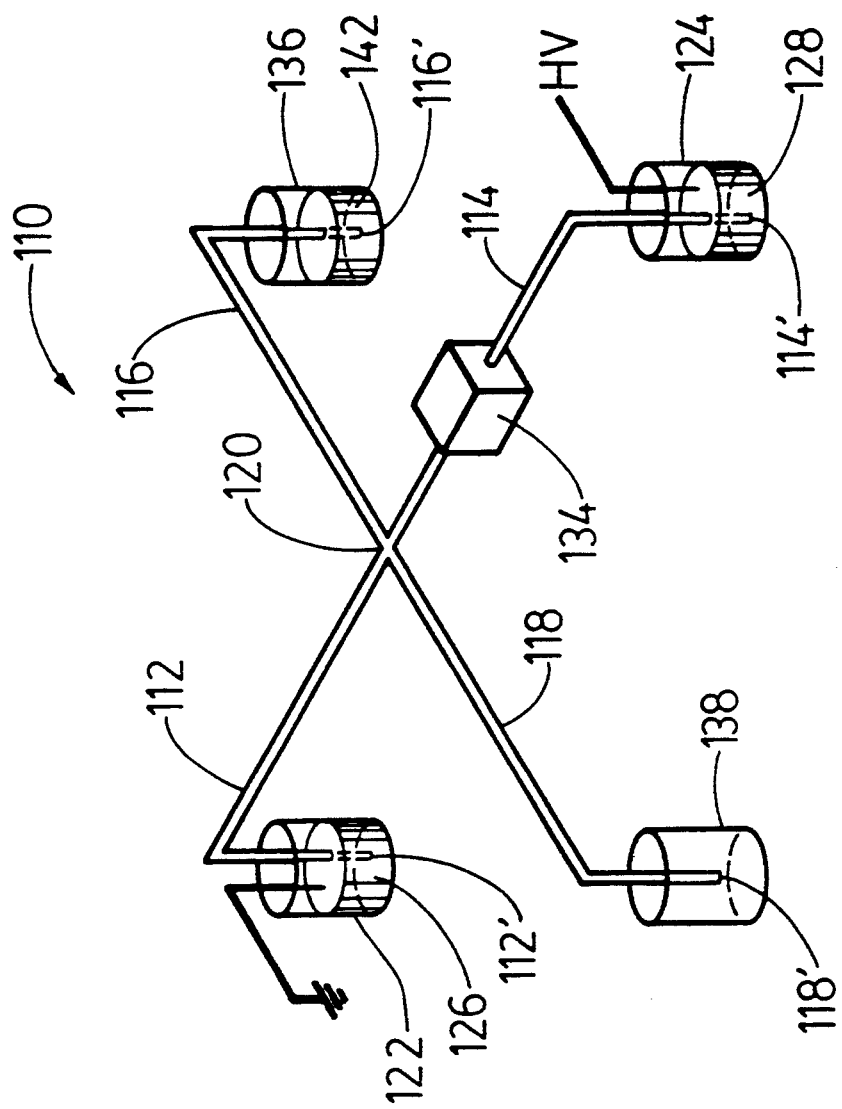
FIG._6.

ON-COLUMN DERIVATIZATION IN CAPILLARY ELECTROPHORESIS

This application is a continuation-in-part application of U.S. patent application Ser. No. 07/235,953, now abandoned, filed Aug. 24, 1988 by Richard N. Zare et al.

BACKGROUND OF THE INVENTION

This application relates in general to separation techniques such as capillary electrophoresis and in particular, to apparatus and method for on-column derivatization in capillary electrophoresis.

Capillary electrophoresis (CE) is rapidly emerging as one of the separation methods of choice in resolving a complex mixture into its constituents (see Jorgenson et al., *Science* 1983, 222, 266; Gordon et al., *Science* 1988, 242, 224; Ewing et al., *Anal. Chem.*, 1989, 61, 292A). In this procedure an electric field is applied across a capillary structure with typical dimensions of 2–200 $\mu$m inside diameter and 10–100 cm length. The medium is an electrolyte or a gel. Because the volumes are small, typically nanoliters of injected sample, a major challenge is to find suitable detection schemes. In past work, many detection schemes have been used, such as optical absorption (see Lauer et al., *Anal. Chem.*, 1986, 58, 166), optical fluorescence (see Gassman et al., *Science*, 1985, 230, 813), electrochemical (see Wallingford et al., *Anal. Chem.*, 1987, 59, 1762), conductimetric detection (see Huang et al., *Anal. Chem.*. 1987, 59, 2747), radioactivity (see Pentoney et al., *Chromatog.*, 1989, 4809, 259, refractive index change (see Bruno et al., *Appl. Spec.*, 1991, 45, 462, and mass spectrometry (see Olivares et al., *Anal. Chem.*, 1987, 60, 1230). In each of these procedures, it may be advantageous to attach to the molecular constituent to be detected a label or tag that aids/enables its detection. Examples are labels for fluorescence, absorption, electrochemical detection and radioactivity.

Frequently, the sample is derivatized off-column prior to being injected. In such pre-separation derivatization schemes, usually the sample to be separated is mixed with a labeling agent or compound in a vial where the compound or agent would react chemically with the sample to label or tag the sample. Such method of labeling or tagging is disadvantageous. Small samples will become diluted by the procedure since, for convenient handling, the vials used cannot be too small. After the labeling or tagging process has been completed, a portion of the labeled sample is then injected into a capillary column for separation. Thus, pre-column labeling requires two or more steps before the labeled sample is ready for separation. Post-column separation techniques have also been used, such as in U.S. Pat. No. 4,729,947 to Middendorf et al. Post-column labeling techniques share the same disadvantages as pre-column labeling techniques.

In view of the above-described drawbacks of off-column type derivatization techniques, on-column derivatization for fluorescence detection using a specially built T-shaped or "cross"-shaped structure in the capillary is proposed in U.S. patent application Ser. No. 07/235,953, filed Aug. 24, 1988 by Richard N. Zare et al., which is incorporated herein in its entirety by reference. See also the article entitled "On-Line Connector for Microcolumns: Application to the On-Column o-Phthaldialdehyde Derivatization of Amino Acids Separated by Capillary Zone Electrophoresis," by Pentoney et al., *Anal. Chem.*, 1988, 60:2625–2629.

Another type of on-column derivatization technique is disclosed in a poster presentation by U. R. Tjaden et al., entitled "On-Line Derivatization and High Performance Capillary Electrophoresis," in the Thirteenth Symposium on Column Liquid Chromatography, Stockholm, Sweden, Jun. 25–30, 1989. In the technique proposed by Tjaden et al., a labeling reagent is added to the electrophoresis buffer in the capillary before the sample to be derivatized is introduced into the capillary column. Such technique also has a number of disadvantages. First, if fluorescent detection is used, the reagent present throughout the buffer in the capillary will cause background fluorescence which degrades the signal-to-noise ratio of the fluorescence detector. Furthermore, the reagent used must be carefully chosen so that the background fluorescence caused by the reagent will not be so high as to render fluorescence detection impossible. This severely limits the type of reagent that can be used and is undesirable.

None of the above-described off-column or on-column techniques is entirely satisfactory. It is therefore desirable to provide an improved on-column derivatization scheme in which the above-described difficulties are alleviated.

In particular, it is desirable to provide an improved on-column derivatization scheme where the unreacted reagent, dye or any other labeling compound would not reach the detector.

SUMMARY OF THE INVENTION

One aspect of the invention is based on the recognition that, by providing through an inlet end of the capillary, a plug of a sample and a labeling reagent, and by causing the reagent and the sample to react in the capillary to label the sample, an improved on-column derivatization scheme is achieved whereby difficulties encountered in conventional systems are avoided or alleviated.

One aspect of the invention is directed towards a method for electrophoretic separation in the capillary containing an electrophoretic separation medium and having an inlet end and an other end. The method comprises providing through said inlet end, a plug of a sample, and a labeling reagent that will react chemically with a sample to label the sample in order to render at least a component of the sample detectable. The labeling reagent and the sample are then caused to react in the capillary to label the sample. If electrophoretic separation is to be carried out after the sample is labeled, an electrical potential is then applied across the labeled sample and the medium to cause the sample to migrate towards the other end of the capillary and to separate the sample in the separation medium into its components. The detectable component is then detected.

Another aspect of the invention is directed towards an apparatus for electrophoretic separation comprising a capillary having an inlet and another end and an electrophoretic separation medium in the capillary. The apparatus further comprises means for providing through the inlet end of the capillary a plug of a sample and a labeling reagent that will react chemically in the capillary with the sample to render at least the labeled component of the sample detectable. The apparatus further comprises means for causing the labeling reagent and the sample to react in the capillary to label the sample. If electrophoretic separation is desired after the labeling process, the apparatus further comprises means for applying an electrical potential across the labeled sample and the medium to cause the sample to migrate towards the other end of the capillary and to separate the sample in the separation medium into its components; and the apparatus further comprises means for detecting the detectable components.

Yet another aspect of the invention is directed towards a solid-phase reactor for tagging of samples in capillary electrophoresis. The reactor comprises a capillary tube with inside cross-sectional dimensions less than about 300 microns, an electrophoretic separation medium in the tube, and a solid reagent in the tube. The reagent is suitable for reacting chemically with samples in order to render predetermined portions of the samples detectable in electrophoresis. The reactor further comprises a means for immobilizing the reagent in the tube and means for providing a plug of sample in the tube to react with the reagent.

BRIEF DESCRIPTION OF THE DRAWINGS

FIG. 2 is a schematic diagram of a dye solution and a capillary with one end inserted into the die solution to perform liquid plug derivatization in the capillary to illustrate one aspect of the invention.

FIG. 3 is a cross-sectional view of a portion of a capillary with a solid reagent to illustrate another aspect of the invention.

FIG. 4 shows an electropheorogram of three different amino acids that have been coupled to carboxytetramethylrhodaminesuccinimidylester (CTMRSE).

FIG. 5 is a schematic diagram of a capillary isotachoelectrophoretic system useful for illustrating the invention.

FIG. 6 is taken from a figure in Ser. No. 07/235,953 to illustrate one scheme of on-column derivatization.

DETAILED DESCRIPTION OF THE PREFERRED EMBODIMENT

Figure 1:
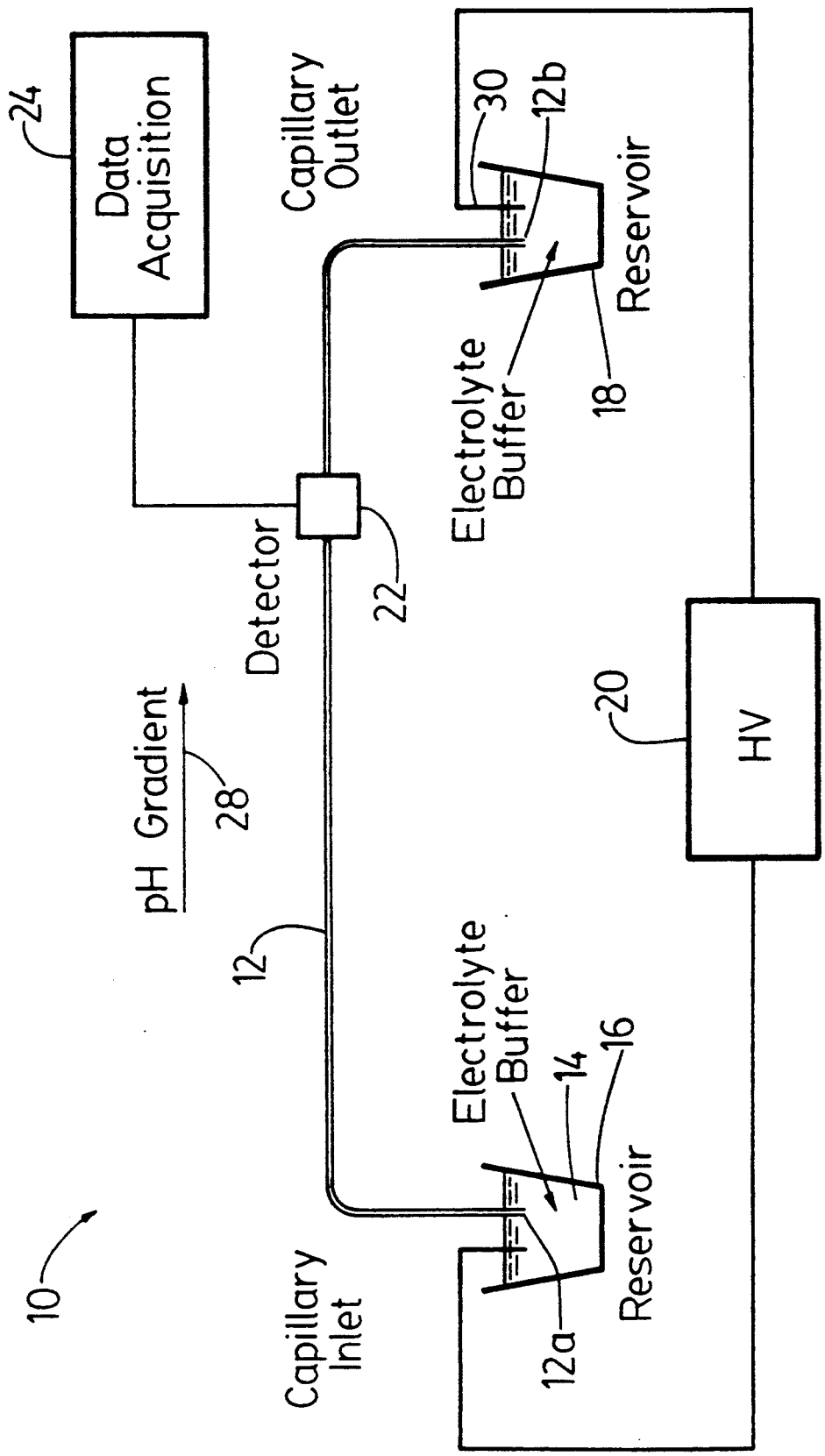
FIG. 1 is a schematic diagram of a capillary zone electrophoretic system useful for illustrating the invention.

FIG. 1 is a schematic view of a capillary electrophoretic system useful for illustrating the invention. As shown in FIG. 1, apparatus 10 includes a capillary tube 12 with an inlet end 12a and an outlet end 12b. An electrolyte buffer 14 is supplied to the tube to end 12a from a reservoir 16. The electrolyte buffer which exits from outlet end 12b is collected from reservoir 18. A high voltage is applied between the two reservoirs, causing the electrolyte to move from reservoir 16 through inlet end 12a, capillary tube 12, and end 12b to exit in the reservoir 18. The high voltage is applied by a voltage supply 20. As is known in conventional capillary electrophoresis, a sample is introduced into the inlet end 12a, such as by dipping end 12a for a short time into a sample and applying a voltage across the tube to move a small portion of the sample into the tube. The end 12a is then dipped in the reservoir 16, where the portion of the sample is then carried under the influence of the electric field through tube 12 towards end 12b. As is also known in the electrophoretic art, different components of the sample may move with different speeds in tube 12, causing the components to separate along the length of the tube. These components are detected by detector 22 when the components pass the detector. Signals from detector 22 are sent to a data acquisition system 24 for analysis and recording.

If isoelectric focusing of the sample components is desired, a pH gradient is applied between the buffers in reservoir 16 and a buffer in reservoir 18. The manner in which such pH gradient along arrow 28 is applied is known to those skilled in the art and therefore will not be described in detail here. For a more detailed description of isoelectric focusing, please see the article entitled "Capillary Isoelectric Focusing of Proteins in Uncoated Fused-Silica Capillaries Using Polymeric Additives," by Mazzeo et al., *Anal. Chem.*, 1991, 63:2852–2857. Similarly, a concentration gradient can also be applied across the medium.

As indicated above, to enhance the detectability of the sample components separated in the electrophoretic process, the sample injected into the capillary 12 is preferably labeled by reacting the sample with a labeling reagent. FIG. 2 illustrates one system for labeling the sample. For simplicity, identical components in the different figures of this application are labeled by the same numerals. As shown in FIG. 2, capillary 12 contains a buffer 14. The inlet end 12a of the capillary is dipped into a dye solution 32 containing dye molecules 34. A plug of analyte or sample was previously injected into end 12a, so that when end 12a is dipped into the dye solution, hydrostatic pressure causes dye solution to enter end 12a, whereupon the dye molecules 34 would diffuse into the analyte region 36 to form an analyte mixture with the dye molecules. To aid the mixing of the dye molecules and the sample or analyte, an electric field may be applied between the dye solution 32 and buffer 14 by means of electrode 38 and the electrode 30 in reservoir 18 of FIG. 1. The dye molecules then react chemically with components of the sample or analyte in zone 36 whereby sample components are thereby labeled or tagged for subsequent detection. To speed up the chemical reaction between the dye molecules and the sample, heat or radiation (optical or otherwise) may be applied along arrows 40.

After the chemical reaction between the dye molecules and the analyte or sample has been completed, end 12a of the capillary is then removed from the dye solution and dipped into buffer 14 of FIG. 1 and high voltage is applied by power supply 20 between reservoirs 16 and 18 to carry out capillary zone electrophoretic separation in the manner described above. The labeled sample or analyte components are then detected by detector 22 by any one of the mechanisms referred to above as well as other processes. Preferably, the electric field applied through electrode 38 is such as to cause adequate mixing of the dye molecules and the sample or analyte without causing any substantial separation of the sample.

In the process described above, the reagent is introduced into end 12a by means of hydrostatic or pressure difference. Alternatively, the dye may be introduced by means of electrokinetic injection, such as by applying a voltage of the order of one to several kilovolts for a short time period between electrode 38 and the electrode in reservoir 18. Essentially the same process as that described above for injecting the die may be used for injecting the analyte or sample into end 12a of the capillary.

Instead of introducing the sample first followed by the dye solution, the dye solution may be first injected before the injection of the sample. It is also possible to introduce a second plug of sample after a first plug of sample followed by the dye solution have both been introduced into end 12a of the capillary shown in FIG.

2. Preferably, the relative migration speed of the sample and the labeling reagents is first determined, and whichever one that migrates at a slower speed is introduced first into the capillary followed by the other with higher migration speed, such as under the influence of an electric field. All such possibilities are featured within the scope of the invention. A suitable solvent for the labeling reagent is DMF.

Unlike the system proposed by Tjaden et al. referenced above, the system of this invention is less limited as to the type of possible labeling reagents so that a wide variety of reagent may be used, including fluorophores. Because of the high background fluorescence of fluorophores, it will be difficult to employ labeling reagents such as fluorphores in the scheme proposed by Tjaden et al.

FIG. 3 is a schematic view illustrating a second embodiment employing a solid reagent for labeling the sample or analyte. As shown in FIG. 3, a solid reagent 50 is immobilized near end 12a of capillary 12 by means of two frits 52. Frits 52 may be made of a porous material made, for example, of glass. A non-absorbing/non-fluorescing native analyte or sample is introduced along arrow 54 by any one of a number of injection mechanisms such as pressure difference or electrokinetic injection. Preferably, the analyte or sample is caused to migrate through the first frit 52 close to end 12b and to mix with reagent 50 by an electric field (not shown) applied in a manner similar to that in FIG. 2. The analyte or sample is then caused to react chemically with reagent 50 in order to label or tag components of the sample or analyte. Again, heat or radiation may be applied to speed up the reaction, along arrows 40. After the sample has been labeled or tagged, end 12a of the capillary may be dipped into buffer 14 of FIG. 1 and high voltage applied by means of power supply 20 to perform the capillary zone electrophoretic separation. Labeling reagent solution less than about 250 nL may be used. The derivatization scheme of this invention may be applicable in capillaries less than 300 microns in inside cross-sectional dimensions.

While the embodiments of FIGS. 1-3 have been described by reference to capillary zone electrophoresis by employing a fluid electrolyte, it will be understood that essentially the same system may be applied for on-column derivatization and sample separation and detection if capillary 12 is filled with a gel medium instead of a fluid electrolyte.

In FIG. 3, of the two frits 52, the frit that is closer to end 12a may be omitted so that reagent 50 may be retrieved from the capillary in order to either replace the reagent by a fresh batch after a number of derivatizations and separations or replaced by a different reagent when it is desirable to change the detection scheme. In other words, only one frit, the one further away from end 12a than the reagent 50, is adequate for immobilizing the reagent in the capillary and preventing the reagent from being moved down the capillary by an electric field applied in the mixing or separation process.

In the preferred embodiment, the labeling reagent is selected so that it is electrically charged to an opposite state from that of the labeled sample, so that when an electrical potential is applied across the labeled sample and the separation medium, the sample components will migrate towards end 12b while the excess reagent will migrate towards end 12a instead, such as would be the case in gel electrophoresis. Where capillary 12 contains a fluid electrolyte, the labeling reagent is preferably selected so that, in addition to being charged to an opposite electrical state from the labeled sample, the electrophoretic migration speed of the reagent is preferably higher than the electroosmotic flow rate of the medium under the same electric field, so that the excess labeling reagent will flow out of end 12a while the labeled end sample is migrating towards end 12b. This feature automatically cleanses the separation medium of the excess reagent so that a capillary may be reused for the next operation without requiring a separation cleansing process.

FIG. 4 shows an electropheorogram of three different amino acids that have been coupled to carboxytetramethylrhodamine succinimidylester (CTMRSE). The separation shown in FIG. 4 is obtained by gravity injecting into the CE column a 10 nL mixture or arginine (17 mM), serine (37 mM), and glutamate (24 mM) dissolved in 0.2M carbonate buffer (pH 9.2). A 10 nL "plug" of $10^{-7}$M CTMRSE (dissolved in DMF) is then gravity injected into the column. A second 10 nL gravity injection of the above amino acid mixture is made. After allowing ten minutes for the derivatization reaction to occur, an electrophoretic separation is performed (20 kV, 35 mM sodium borate buffer, pH 9.2) using a CE system with multichannel laser-induced fluorescence detection (12).

This demonstration shows the possibility of adding a fluorescent tag to an amino acid. Many other possibilities exist.

FIG. 5 is a schematic view of an isotachophoretic system wherein the on-column derivatization scheme described above in reference to FIGS. 2 and 3 may be employed. As shown in FIG. 5, the sample may be injected through injection port I. Where the labeling reagent is a dye solution, it may be injected through port I also. Both the sample and the reagent may be injected by means of electrokinetic or pressure difference injection, in the manner similar to that described above in reference to FIG. 2, where the sample and the reagent are allowed to react before the separation process. If the reagent used is a solid, side tube 80 may contain reagent 50 and be constructed in the manner similar to the portion of capillary 12 shown in FIG. 3, where the solid reagent 50 is immobilized by one or more frits 52. Alternatively, the solid reagent 50 and frits 52 may be located in the section of the capillary column C downstream but immediately adjacent to side tube 80, as indicated by location 82. Again, the tagging process performed in the isotachophoretic scheme of FIG. 5 is similar to that described above in reference to FIG. 3. Side tube 80 may be replaced by a proper injection valve.

From the above description, it will be evident to those skilled in the art that the objectives of this invention are achieved. Since the amount of labeling reagent employed used may be small and just enough for labeling a sample, less reagent needs to be used compared with, for example, the scheme of Tjaden et al. where the reagent is present in the entire column. The handling of the sample is much simplified. The labeling of the sample and the subsequent separation and detection may be carried out in one step instead of two or more steps as in off-column derivatization schemes. Since the derivatization occurs in the capillary column, the sample is not unduly diluted in the process compared to off-column derivatization schemes. For very small samples such as in microanalysis of biostructures such as individual cells, the amount of reagents used can be proportionally reduced. In the scheme of FIG. 2, the injection procedure is controlled such that the amount of dye introduced may be small and just adequate for labeling the small sample in the capillary. In the scheme of FIG. 3, only the portion of the reagent that is used in labeling the analyte or sample will be carried along with the sample during the subsequent separation while the excess reagent will remain immobilized. Because the labeling reaction occurs locally in a small region within the capillary, high local concentrations of reagents is possible. This is particularly advantageous since the speed of the labeling reaction depends on the concentration of both the reagents and of the sample. By localizing the reaction to a small zone in the capillary, high local concentration of reagents is possible, allowing for fast kinetics and high reaction yield. In the scheme of FIG. 3, the excess reagent does not cause separation problems when recovering the sample product. By choosing a labeling reagent that is oppositely charged from the labeled sample, the excess reagent exits from the inlet end of the capillary and also does not cause separation problems when recovering the separated sample components. The overall process of derivatization, separation and detection can be carried out much more rapidly as compared to conventional methods.

While in FIG. 3, the reagent 50 and frit 52 are shown close to end 12a of the capillary, it will be understood that the reagent and the frit may be located in an interior portion of the capillary much further away from either end 12a or 12b.

This application incorporates a portion of U.S. patent application Ser. No. 07/235,953, filed Aug. 24, 1988 by Zare et al. The portion incorporated is set forth below in reference to FIG. 6 of this application (FIG. 1 of Ser. No. 235,953).

FIG. 6 is a schematic view of an electrophoretic system for performing CZE processes employing device 110 to illustrate the preferred embodiment of the invention. As shown in FIG. 6, device 110 comprises a main capillary tube which includes two portions 112, 114, and a second capillary tube comprising two portions 116, 118 where the two tubes are connected at connection 120 in a manner so that a second fluid flowing in the second tube will mix with a first fluid flowing in the main capillary tube. The two ends 112', 114' of the main capillary tube are in containers 122, 124 which may be beakers. Containers 122, 124 contain electrolytes 126, 128 respectively. An electrical potential is applied between the two electrolytes as shown in FIG. 6, causing the electrolyte 126 to flow through portion 112 and then portion 14 of the main capillary to container 124. During its flow, the constituents of the electrolyte 126 are detected by detector 134.

To aid the separation and analysis in the CZE process, a second fluid is introduced and mixed with the electrolyte 126 during its flow through portion 114 by means of the second capillary tube. The ends 116', 118' of the second capillary are placed in containers 136, 138 respectively. A liquid 142 is placed in container 136 and container 136 is placed at a higher elevation than container 138. After liquid 142 is introduced in the portion 116, it will flow towards connection 120 to portion 118 and is subsequently discharged into container 138. Since the space enclosed by the second capillary is connected to the space enclosed by the main capillary at connection 120, a small portion of the liquid 142 will become mixed with the portion of the electrolyte in the main capillary and the mixture will flow through portion 114.

Thus, separation can be enhanced and such separation can be detected by detector 34.

FIG. 6 can be modified slightly for chromotographic separation. Thus instead of using an electrical means, the fluid in portions 112, 114 of the main capillary as well as the liquid 142 in the second capillary 116 may be moved by pressure generating devices instead of electrical means as in FIG. 6. Such scheme is shown in FIG. 2 of the related application Ser. No. 07/235,953. The pressure generating devices are pumps P1, P2 of FIG. 2 of such application.

While the invention has been described above by reference to various embodiments, it will be understood that modifications may be made without departing from the scope of the invention which is to be limited only by the appended claims.

What is claimed is:

1. A method for electrophoretic separation of a sample in a capillary containing an electrophoretic separation medium and having an inlet end and another end, comprising:

introducing into the capillary an electrophoretic separation medium, said medium containing substantially no reagent for labelling the sample for detection;

providing through said inlet end of the capillary a sample;

providing through said inlet end of the capillary a substance before or after the sample is provided, so that the sample and the substance will react chemically in the capillary, said sample having components, thereby rendering at least a component of the sample detectable;

causing said substance and the sample to react in the capillary;

applying an electrical potential across the labelled sample and the medium to cause the sample to migrate towards the end of the capillary and to separate the sample in the separation medium into its components; and detecting said detectable component.

2. A method for electrophoretic separation of a sample in a capillary containing an electrophoretic separation medium and having one or more inlets and an end, comprising:

introducing into the capillary an electrophoretic separation medium, said medium containing substantially no substance for changing detectability of the sample;

providing through an inlet of the capillary a sample;

providing through an inlet of the capillary a substance before or after the sample is provided, so that the sample and substance will react chemically in the capillary, said sample having components, thereby rendering at least a component of the sample detectable;

causing said substance and the sample to react in the capillary;

applying an electrical potential across the labelled sample and the medium to cause the sample to migrate towards the end of the capillary and to separate the sample in the separation medium into its components; and detecting said detectable component, said method further comprising establishing a concentration gradient of a species across the medium.

3. A method for electrophoretic separation of a sample in a capillary containing an electrophoretic separation medium and having one or more inlets and an end, comprising:

introducing into the capillary an electrophoretic separation medium, said medium containing substantially no substance for changing detectability of the sample;

providing through an inlet of the capillary a sample;

providing through an inlet of the capillary a substance before or after the sample is provided so that the sample and substance will react chemically in the capillary, said sample having components, thereby rendering at least a component of the sample detectable;

causing said substance and the sample to react in the capillary;

applying an electrical potential across the labelled sample and the medium to cause the sample to migrate towards the end of the capillary and to separate the sample in the separation medium into its components;

detecting said detectable component and causing excess substance to migrate towards an inlet of the capillary.

4. The method of claim 3, wherein said separation medium is a fluid electrolyte, and wherein the migration speed of the excess substance is higher than the electroosmotic flow rate of the medium towards the end of the capillary, so that said electrical potential applying step causes excess substance to flow towards the inlet end of the capillary.

5. An apparatus for electrophoretic separation of a sample comprising:

a capillary having an inlet end and another end;

an electrophoretic separation medium in said capillary, said medium containing substantially no substance for changing detectability of the sample;

means for providing through said inlet end of the capillary a sample;

means for providing through said inlet end of the capillary a substance so that the sample and the capillary a substance provided will react chemically in the capillary, said sample having components, thereby rendering at least a component of the sample detectable;

means for causing said substance and the sample to react in the capillary;

means for applying an electrical potential across the reacted sample and the medium to cause the sample to migrate towards the other end of the capillary and to separate the sample in the separation medium into its components; and means for detecting said detectable component.

6. An apparatus for electrophoretic separation of a sample comprising:

a capillary having one or more inlets and an end;

an electrophoretic separation medium in said capillary, said medium containing substantially no substance for changing detectability of the sample;

means for providing through an inlet of the capillary a sample;

means for providing through an inlet of the capillary a substance so that the sample and the substance provided will react chemically in the capillary, thereby rendering at least a component of the sample detectable;

means for causing said labelling substance and the sample to react in the capillary;

means for applying an electrical potential across the labelled sample and the medium to cause the sample to migrate towards the end of the capillary and to separate the sample in the separation medium into its components; and means for detecting said detectable component, said apparatus further comprising means for establishing a concentration gradient of a species across the medium and for isoelectric focusing the sample components.

7. An apparatus for electrophoretic separation of a sample comprising:

a capillary having one or more inlets and another end;

an electrophoretic separation medium in said capillary, said medium containing substantially no substance for changing detectability of the sample;

means for providing through an inlet of the capillary a sample;

means for providing through an inlet of the capillary a substance so that the sample and the substance will react chemically in the capillary, said sample having components, thereby rendering at least a component of the sample detectable;

means for causing said substance and the sample to react in the capillary;

means for applying an electrical potential across the labelled sample and the medium to cause the sample to migrate towards the end of the capillary and to separate the sample in the separation medium into its components; and means for detecting said detectable component; and means for causing the substance to migrate towards an inlet of the capillary.

8. The apparatus of claim 7, wherein the substance is electrically charged to an opposite state from that of the labelled sample so that the electrical potential applied by said electrical potential applying causes excess substance to flow towards an inlet of the capillary.

9. A method for on-column derivatization of a sample for electrophoretic separation, comprising:

introducing into a capillary an electrophoretic separation medium, said capillary having an inlet, said medium containing substantially no substance for changing detectability of the sample;

providing through said inlet of the capillary a sample;

providing through said inlet of the capillary a substance before or after the sample is provided, so that the sample and the substance will react chemically in the capillary, thereby rendering at least a portion of the sample detectable; and causing said substance and the sample to react in the capillary before any substantial separation of the sample.

10. The method of claim 9, wherein said providing steps introduce the sample or substance by means of pressure difference.

11. The method of claim 9, wherein said providing steps introduce the sample or substance by electrokinetic injection.

12. The method of claim 9, wherein said substance is a solution, and said providing steps introduce the sample first, followed by said substance.

13. The method of claim 12, wherein said providing steps introduce a second sample after the introduction of said substance.

14. The method of claim 9, wherein said labelling substance providing step introduces fluorophores.

15. The method of claim 9, wherein the inside cross sectional dimensions of the capillary are less than about 300 microns and said sample providing step introduces a plug of sample that is less than 100 nL in volume.

16. The method of claim 9, wherein said substance is a solution, said causing step including the step of mixing the substance and the sample.

17. The method of claim 16, wherein said mixing step includes the application of an electric field to the sample and the substance.

18. The method of claim 9, wherein said causing step includes the application of heat or radiation to the sample and the substance.

19. The method of claim 9, said providing steps introduce the substance first, followed by said sample.

20. A method for on-column derivatization of a sample for electrophoretic separation, comprising:
    introducing into a capillary an electrophoretic separation medium, said capillary having one or more inlets and an end, said medium containing substantially no substance for changing detectability of the sample;
    providing through an inlet of the capillary a sample;
    providing through an inlet of the capillary a substance before or after the sample is provided, so that the sample and the substance will react chemically in the capillary, thereby rendering at least a portion of the sample detectable; and
    causing said substance and the sample to react in the capillary before any substantial separation of the sample, wherein said causing or providing steps cause the sample and substance to migrate in the capillary, said providing steps including determining the relative migration speed of the sample and the substance and introducing first whichever one that migrates at a slower speed followed by the other.

21. A method for on-column derivatization of a sample for electrophoretic separation, comprising:
    introducing into a capillary an electrophoretic separation medium, said capillary having one or more inlets, said medium containing substantially no substance for changing detectability of the sample;
    providing through an inlet of the capillary a sample;
    providing through an inlet of the capillary a substance before or after the sample is provided, so that the sample and substance will react chemically in the capillary, thereby rendering at least a portion of the sample detectable; and
    causing said substance and the sample to react in the capillary before any substantial separation of the sample, wherein said substance providing step introduces a solution of the substance that is less than 250 nL in volume.

22. A method for on-column derivatization of a sample for electrophoretic separation, comprising:
    introducing into a capillary an electrophoretic separation medium, said capillary having one or more inlets, said medium containing substantially no substance for changing detectability of the sample;
    providing through an inlet of the capillary a sample;
    providing through an inlet of the capillary a substance before or after the sample is provided, so that the sample and substance will react chemically in the capillary, thereby rendering at least a portion of the sample detectable; and
    causing said substance and the sample to react in the capillary before any substantial separation of the sample, wherein said labelling substance providing step includes immobilizing a solid substance in the capillary at or near an inlet, said solid substance being selected so as to render a predetermined portion of the sample detectable.

23. A method for on-column derivatization of a sample for electrophoretic separation, comprising:
    introducing into a capillary an electrophoretic separation medium, said capillary having one or more inlets, said medium containing substantially no substance for changing detectability of the sample;
    providing through an inlet of the capillary a sample;
    providing through an inlet of the capillary a substance before or after the sample is provided, so that the sample and substance will react chemically in the capillary, thereby rendering at least a portion of the sample detectable; and
    causing said substance and the sample to react in the capillary before any substantial separation of the sample, and causing the reacted sample and excess substance to move in opposite directions under the influence of an electric field applied along the length of the capillary.

24. The method of claim 23, wherein said separation medium is a fluid electrolyte, and wherein said selecting step selects a substance whose migration speed is higher than the electroosmotic flow rate of the medium under the same electric field.

25. An apparatus for on-column derivatization in electrophoretic separation of a sample in a capillary having an inlet end and another end and containing an electrophoretic separation medium, said apparatus comprising:
    device for introducing an electrophoretic separation medium in said capillary, said medium containing substantially no substance for changing detectability of said sample;
    means for providing through the inlet end of the capillary a sample;
    means for providing through said inlet end of the capillary a substance that will react chemically in the capillary with the sample, thereby rendering at least a portion of the sample detectable; and
    means for causing said substance and the sample to react in the capillary before any substantial separation of the sample.

26. The apparatus of claim 25, wherein one or both of said providing means include means for applying pressure difference.

27. The apparatus of claim 25, wherein one or both of said providing means include means for electrokinetic injection.

28. The apparatus of claim 25, wherein said means for providing said substance provides fluorophores.

29. The apparatus of claim 25, wherein the inside cross sectional dimensions of the capillary are less than about 300 microns and said means for providing sample provides a plug of sample that is less than about 250 nL in volume.

30. An apparatus for on-column derivatization in electrophoretic separation of a sample in a capillary having one or more inlets and an end and containing an electrophoretic separation medium, said apparatus comprising:
    device for introducing an electrophoretic separation medium in said capillary, said medium containing substantially no substance for changing detectability of said sample;

means for providing through an inlet of the capillary a sample;

means for providing through an inlet of the capillary a substance that will react chemically in the capillary with the sample, thereby rendering at least a portion of the sample detectable; and means for causing said substance and the sample to react in the capillary before any substantial separation of the sample, wherein said means for providing substance provides a solution of the substance that is less than about 250 nL in volume.

31. A method for on-column derivatization in electrophoretic separation of a sample in a capillary having one or more inlets and an end and containing an electrophoretic separation medium, said apparatus comprising:

device for introducing an electrophoretic separation medium in said capillary, said medium containing substantially no substance for changing detectability of said sample;

means for providing through an inlet of the capillary a sample;

means for providing through an inlet of the capillary a substance that will react chemically in the capillary with the sample, thereby rendering at least a portion of the sample detectable; and means for causing said substance and the sample to react in the capillary before any substantial separation of the sample, and means for causing excess substance to move in a direction opposite to that of the reacted sample under the influence of an electric field applied along the length of the capillary.

32. The method of claim 31, wherein said separation medium is a fluid electrolyte, and wherein the migration speed of the substance is higher than the electroosmotic flow rate of the medium under the same electric field.

33. A solid-phase reactor for tagging of samples in capillary electrophoresis comprising:

a capillary tube with inside cross sectional dimensions less than about 300 microns;

an electrophoretic separation medium in said tube;

a solid substance in the tube, said substance being suitable for reacting chemically with samples in order to render predetermined portions of said samples detectable in electrophoresis;

means for immobilizing said substance in the tube; and means for providing a plug of sample in the tube to react with said substance.

34. The reactor of claim 33, said substance including fluorophores.

35. The reactor of claim 33, said immobilizing means including one or more frits in the tube.

36. A method for on-column derivatization of a sample for electrophoretic separation, comprising:

introducing into a capillary an electrophoretic separation medium, said capillary having one or more inlets, said medium containing substantially no substance for changing detectability of the sample;

providing through an inlet of the capillary a sample;

providing through an inlet of the capillary a substance before or after the sample is provided, so that the sample and substance will react chemically in the capillary, thereby rendering at least a portion of the sample detectable; and causing said substance and the sample to react in the capillary before any substantial separation of the sample, wherein said substance providing step includes immobilizing a substance in the capillary at or near an inlet, said substance selected so as to render a predetermined portion of the sample detectable.

37. A reactor for tagging of samples in capillary electrophoresis comprising:

a capillary tube with inside cross sectional dimensions less than about 300 microns;

an electrophoretic separation medium in said tube;

a substance immobilized in the tube, said reagent being suitable for reacting chemically with samples in order to render predetermined portions of said samples detectable in electrophoresis; and means for providing a sample in the tube to react with said substance.

* * * * *

UNITED STATES PATENT AND TRADEMARK OFFICE
CERTIFICATE OF CORRECTION

PATENT NO. : 5,318,680
DATED : June 7, 1994
INVENTOR(S) : Harvey A. Fishman et al It is certified that error appears in the above-indentified patent and that said Letters Patent is hereby corrected as shown below:

In Column 13, Line 12 in Claim 31:
    replace "A method for on-column derivatization in electro-" with:

--An apparatus for on-column derivatization in electro- --

Signed and Sealed this

Twenty-ninth Day of November, 1994

Attest:

BRUCE LEHMAN

*Attesting Officer*    *Commissioner of Patents and Trademarks*